United States Patent [19]

Wild

[11] 3,979,383
[45] Sept. 7, 1976

[54] PURIFICATION PROCESS FOR 7-AMINOCEPHALOSPORINS

[75] Inventor: Gene M. Wild, Indianapolis, Ind.

[73] Assignee: Eli Lilly and Company, Indianapolis, Ind.

[22] Filed: Mar. 7, 1975

[21] Appl. No.: 556,508

[52] U.S. Cl. .............................. 260/243 C; 424/246
[51] Int. Cl.² ........................................ C07D 501/12
[58] Field of Search ................................ 260/243 C

[56] References Cited
UNITED STATES PATENTS

| | | | |
|---|---|---|---|
| 3,207,755 | 9/1965 | Abraham et al. | 260/243 C |
| 3,219,662 | 11/1965 | Abraham et al. | 260/243 C |
| 3,467,654 | 9/1969 | McCormick | 260/243 C |

Primary Examiner—Nicholas S. Rizzo
Assistant Examiner—Jose Tovar
Attorney, Agent, or Firm—William B. Scanlon; Everet F. Smith

[57] ABSTRACT

Cephalosporin nucleus compounds represented by the formula:

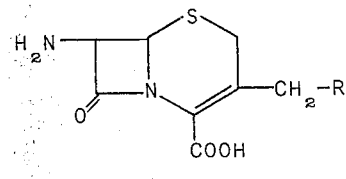

wherein R is for example, acetoxy or a 1-(lower alkyl)-1H-tetrazole-5-yl, a 5-(lower alkyl)-1,3,4-thiadiazole-2-yl or a 5-(lower alkyl)-1,3,4-oxadiazole-2-yl group are purified via chromatography over the hydrophilic polyacrylic matrixed quaternary ammonium anionic exchange resin, Amberlite IRA-458.

5 Claims, No Drawings

PURIFICATION PROCESS FOR 7-AMINOCEPHALOSPORINS

BACKGROUND OF THE INVENTION

Numerous cephalosporin antibiotic compounds having a heterocyclic ring bonded to a sulfur atom attached to the 3-methylene group of the cephalosporin ring system are known. For example, Ryan in U.S. Pat. No. 3,641,021 describes cephalosporin antibiotics substituted in the 3-position with the 1H-tetrazole-5-ylthiomethyl and 1,3,4-thiadiazole-2-ylthiomethyl groups and in the 7-position with the D-phenylglycylamido and D-mandelamido groups. For example, 7-D-mandelamido-3-(5-methyl-1,3,4-thiadiazole-2-ylthiomethyl)-3-cephem-4-carboxylic acid is described by Ryan.

Tokano et al., U.S. Pat. No. 3,516,997, describe other cephalosporin antibiotics having the tetrazole-5-ylthiomethyl, substituted tetrazole-5-ylthiomethyl, 1,3,4-thiadiazole-2-ylthiomethyl, and 1,3,4-oxadiazole-2-ylthiomethyl group in the 3-position.

Further, Crast in U.S. Pat. No. 3,757,014 describes cephalosporin compounds substituted in the 3-position with the 5-hydroxymethyl-1,3,4-oxadiazole-2-ylthiomethyl group. Cephalosporins substituted in the 3'-position with the 2-methyltetrazole-5-ylthiomethyl group are described in U.S. Pat. No. 3,757,015.

The cephalosporin antibiotics described in the aforementioned patents were prepared by reacting 7-aminocephalosporanic acid (7-ACA) with the appropriate heterocyclic thiol. The reaction proceeds via the nucleophilic displacement of the acetoxy group of 7-ACA or of an amino-protected 7-ACA at or near neutral pH to provide the 7-amino-3-heterocyclic-thiomethyl-3-cephem-4-carboxylic acid. For example, 7-ACA is reacted as described in U.S. Pat. 3,641,021 with 5-methyl-1,3,4-thiadiazole-2-thiol to yield 7-amino-3-(5-methyl-1,3,4-thiadiazol-2-ylthiomethyl)-3-cephem-4-carboxylic acid. The 3-thio-substituted nucleus is then N-acylated in the 7-position with the desired acyl derivative of a carboxylic acid to afford the described antibiotics.

The described 7-amino-3-heterocyclic-thiomethyl-3-cephem-4-carboxylic acids are valuable intermediates in the preparation of cephalosporin antibiotics, for example, those described in the above-cited Ryan and Tokano patents. Particularly noteworthy are the antibiotics cefamandole, 7-D-mandelamido-3-(1-methyl-1H-tetrazole-5-ylthiomethyl)-3-cephem-4-carboxylic acid, described by Ryan in U.S. Pat. No. 3,641,021 and the commercial antibiotic, cefazolin, 7-(1H-tetrazole-1-yl)acetamido-3-(5-methyl-1,3,4-thiadiazole-2-ylthiomethyl)-3-cephem-4-carboxylic acid, described by Tokano et al., U.S. Pat. No. 3,516,997.

7-Aminocephalosporanic acid (7-ACA), is a well known cephalosporin nucleus intermediate used in the preparation of many cephalosporin antibiotics, For example, N-acylation of 7-ACA with thiophene-2-acetyl chloride affords the commercial antiobiotic cephalothin.

7-ACA is produced by the N-deacylation of the α-aminoadipamido side chain of cephalosporin C. Cephalosporin C is produced by culturing *Cephalosporium acremonium* or other species of cephalosporium in nutrient media. The N-deacylation of cephalosporin C is carried out with a phosphorus halide, e.g., phosphorus pentachloride, to generate the intermediate imino halide of the side chain. The imino halide is converted to an imino ether which is decomposed to effect the side chain cleavage and provide the cephalosporin nucleus, 7-ACA.

The impurities associated with cephalosporin C of fermentation origin can carry through the N-deacylation reaction and complicate the purification of the 7-ACA product. Impurities of fermentation origin such as polysaccharides, aminoacids and other present difficult isolation and purification problems in the large scale manufacture of 7-ACA of suitable purity for use as an intermediate for antibiotics.

The preparation of the intermediate 7-amino-3-heterocyclicthiomethyl-3-cephem-4-carboxylic acids (hereinafter referred to as 3-substituted nucleus) by the nucleophilic displacement of the acetoxy group of 7-ACA or an N-protected 7-ACA with the heterocyclic thiol is accompanied by the formation of highly colored impurities. These impurities render difficult the purification of the 3-substituted nucleus. Accordingly, in order to obtain the final antibiotic in pharmaceutical purity, either the nucleus is purified by repeated isoelectric precipitation or the final antibiotic product obtained by the acylation of the unpurified 3-substituted nucleus is purified. In the large scale commercial preparation of antibiotics cumbersome and expensive purification procedures are undesirable and uneconomical. Accordingly there is a need in the cephalosporin art for a convenient method for the purification of 7-ACA and the 3-thio-substituted nucleus compounds which avoids multiple recrystallization to achieve pharmaceutical purity.

SUMMARY

This invention relates to a method for purifying certain cephalosporin nucleus compounds. In particular it relates to a purification process for 7-aminocephalosporanic acid and 7-amino-3-heterocyclic-thiomethyl-3-cephem-4-carboxylic acids which comprises ion exchange chromatography over an anion exchange resin having a polyacrylic matrix bearing quaternary trimethylammonium functions. For example, impure and highly colored 7-amino-3-(5-methyl-1,3,4-thiadiazole-2-ylthiomethyl)-3-cephem-4-carboxylic acid is first converted to a water soluble salt such as the sodium, ammonium or other soluble salt at a pH of about 6.5–8.5. A solution of the salt in water is loaded onto the polyacrylic quaternary ammonium resin, IRA-458, in the acetate cycle or other cycle obtained with suitable monovalent anions at about 10 g. per 100 ml. of the gel resin. After loading the resin is washed with water. The nucleus compound is then eluted from the exchange resin with 0.2 to 0.5 molar phosphate buffer or other suitable buffered eluant at about pH 8. The eluate is collected and acidified to precipitate the purified 7-amino-3-(5-methyl-1,3,4-thiadiazole-2-ylthiomethyl)-3-cephem-4-carboxylic acid.

DETAILED DESCRIPTION

According to the method of this invention 7-ACA or a 7-amino-3-heterocyclic-thiomethyl-3-cephem-4-carboxylic acid represented by the formula

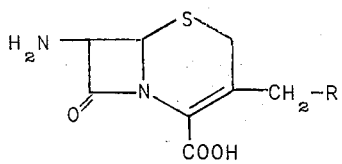

I wherein R is acetoxy or a heterocyclic group selected from the group consisting of

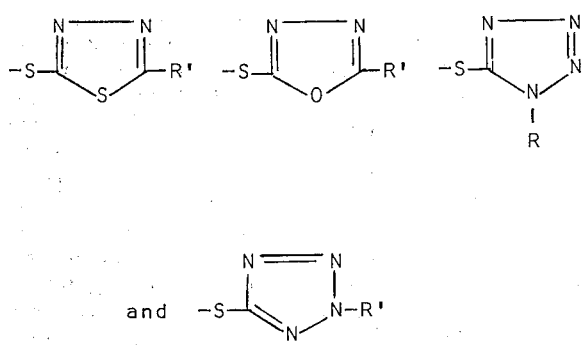

and wherein R' is $C_1$-$C_4$ alkyl;
is purified by chromatography over the quaternary ammonium anion exchange resin, Amberlite IRA-458.

The resin employed is a strongly basic, hydrophilic resin, having a polyacrylic matrix. The functional anionic groups are quaternary ammonium groups. This resin is commercially available from Rohm and Haas Company, Philadelphia, Pa., in the chloride form as clear beads of 16–50 mesh (U.S. Standard Screens).

In the process of this invention an impure cephalosporin nucleus compound of the formual I is dissolved in water at a pH of about 8. The solution is obtained by adding to an aqueous suspension of the nucleus a base such as ammonium hydroxide, sodium hydroxide, potassium hydroxide or other suitable base. Preferably the concentration of the solution is about 5%. The solution is then loaded onto a column packed with IRA-458 preferably in the acetate cycle. The resin is prepared in the acetate cycle by washing the commercial resin in the chloride cycle with an aqueous solution of sodium acetate preferably at a concentration of about 6%. Alternatively an aqueous solution of sodium methanesulfonate can be used to convert the resin to the methanesulfonate cycle. In loading the column a desirable ratio of weight of cephalosporin nucleus to volume of resin is about 10 g. of nucleus compound to about 100 ml of resin volume.

After loading the column with the nucleus solution the column is preferably washed with a volume of water about twice the volume of resin employed. Following the water wash, the cephalosporin nucleus is eluted from the resin with a phosphate buffer of between about 0.2 to 0.5 molar and preferably at about 0.3 to 0.5 molar. Potassium phosphate buffer, 0.44 M pH 8, is a preferred buffer. A solution of ammonium phosphate or other water soluble phosphate adjusted to about pH 8 serves as an alternate eluant buffer. Phosphate buffers are desirable eluants in that the pH can be readily maintained at about pH 8 during the elution. At a pH below about 7.5 the cephalosporin nucleus compound can begin to precipitate from the eluant as it passes through the resin bed. At a pH above about 9.0 the eluant is basic enough to cause some decomposition of the cephalosporin nucleus compound thus lowering the yield obtained in the process. Accordingly, the desired pH of the eluant is between about pH 7.8 and about 8.7 and preferably between about 8.0 and 8.5.

Elution of the column is continued until the effluent fails to become cloudy when acidified to a pH of about 3.1–4.0. The effluent is acidified with stirring to a pH of between about 3.4 and 4.5. The temperature of the effluent during acidification is desirably maintained at about 20° to 25°C. Dilute sulfuric acid or hydrochloric acid are suitable for acidification of the eluate.

The purified cephalosporin nucleus precipitates or crystallizes from the acidified effluent and is separated on a filter or centrifuge. The filter cake or centrifuge cake is washed with deionized water and then with acetone. The washed nucleus is dried at about 70°C. to a white or off white powder.

In general the yield of the purified product obtained off the column is on the order of 75–85% based on the impure cephalosporin nucleus.

Illustrative of the 3-substituted nucleus compounds which can be purified in the process of this invention are 7-aminocephalosporanic acid (7-ACA), 7-amino-3(5-methyl-1,3,4-thiadizole-2-ylthiomethyl)-3-cephem-4-carboxylic acid, 7-amino-3-(5-ethyl-1,3,4-thiadiazole-2-ylthiomethyl)-3-cephem-4-carboxylic acid, 7-amino-3-(5-methyl-1,3,4-oxadiazole-2-ylthiomethyl)-3-cephem-4-carboxylic acid, 7-amino-3-(1-ethyl-1H-tetrazole-5-ylthiomethyl)-3-cephem-4-carboxylic acid, 7-amino-3(2-methyltetrazole-5-ylthiomethyl)-3-cephem-4-carboxylic acid, 7-amino-3-(5-isopropyl-1,3,4-thiadiazole-2-ylthiomethyl)-3-cephem-4-carboxylic acid and 7-amino-3(1-n-butyl-1H-tetrazole-5-ylthiomethyl)-3-cephem-4-carboxylic acid.

The 7-amino-3-heterocyclic-thiomethyl-3-cephem-4-carboxylic acids of the formula I are prepared by reacting 7-aminocephalosporanic acid with the desired lower alkyl substituted heterocyclic thiol. For example, 7-aminocephalosporanic acid is suspended in water and as ammonium hydroxide is added to adjust the pH of the suspension to about 7.5 the 7-ACA dissolves to form a solution. To the solution is added a solution of an excess of 5-methyl-1,3,4-thiadiazole-2-thiol in water at a pH of about 7.0. The mixture is then heated at about 60°–70°C. for about 1–2 hours with stirring. The reaction mixture is acidified with a mineral acid such as sulfuric acid or hydrochloric acid to a pH of about 3.5–4.0 to precipitate the product 7-amino-3-(5-methyl-1,3,4-thiadiazole-2-ylthiomethyl)-3-cephem-4-carboxylic acid. The product is collected by filtration, is washed with water and acetone and is dried.

Alternatively an amino protected 7-ACA, such as N-formyl 7-ACA or 7-(p-nitrobenzyloxycarbonyl)-7-ACA, can be reacted with the desired heterocyclic thiol and the 7-amino protecting group removed from the product to provide the 3-substituted nucleus compound.

The 3-substituted nucleus compounds, prepared as described above for the thiadiazole nucleus, are obtained as solids containing highly colored impurities. Impurities which can be present include unreacted starting materials. desacetyl 7-ACA, and yellow to brown polymeric side products. In the resin process of this invention these side-products including the highly colored brown to dark yellow impurities are effectively removed from the 3-substituted nucleus product. The 3-substituted nucleus product of the formula I is obtaned off the IRA-458 resin in a high state of purity and can be used for acylation without further purification. The practice of this invention provides large quantitites of substantially pure nucleus compounds of the formula I. The necessity of repetitive recrystallizations to achieve the same result on a manufacturing scale is avoided.

The resin employed in the process of this invention is uniquely suited for the purification of the cephalosporin nucleus compounds. An important characteristic displayed by Amberlite IRA-458 resin in this process, is its "low hold up" or low retention of the cephalosporin nucleus. Yields of nucleus of about 75 to 85 percent across the column are generally obtained. In contrast numerous other commercial resins, for example polystyrene resins, either fail to separate the nucleus from impurities or bind the nucleus so strongly that low yields are obtained on elution.

The purity of the cephalosporin nucleus obtained in the process of this invention is determined by comparing the absorption of the sample at 273 nm in the ultraviolet with that of a standard sample. When a 3-heterocyclic-thio-substituted nucleus of the formula I is assayed for percent purity, the sample is further analyzed for 7-aminocephalosporanic acid content and the 7-ACA content of the sample which contributes to the absorbance in the UV assay is subtracted therefrom. The 7-ACA content of the sample is determined on a Beckman model 116 Spectrophotometric Amino Acid analyzer.

The color of the sample is measured at 500 nm in the visible spectrum.

The following example is provided to further illustrate the process of this invention.

EXAMPLE 1

Preparation of purified
7-amino-3-(5-methyl-1,3,4-thiadiazole-2-ylthiomethyl)-3-cephem-4-carboxylic acid.

To a glass-lined reactor containing 1800 l. of deionized water 73 kg of 5-methyl-1,3,4-thiadiazole-2-thiol were added and the reactor was heated with stirring to a temperature of about 75°C. The pH of the mixture was adjusted to pH 6.5 to 7.0 by the addition of concentrated ammonium hydroxide.

In a separate glass-lined vessel containing 800 l. of deionized water were added 141 kg. of 7-aminocephalosporanic acid with stirring and an additional 1200 l. of deionized water were added to the slurry. The slurry was cooled to about 15°C. and the pH was adjusted to about 7.5 with concentrated ammonium hydroxide.

The slurry of 7-ACA, pH 7.5 was added to the reactor containing the 5-methyl-1,3,4-thiadiazole-2-thiol solution and the mixture was stirred at about 65°C. for 70 minutes. During the reaction the pH was maintained at between 6.5 and 7.0 by the addition of concentrated ammonium hydroxide when required.

The reaction mixture is then acidified with stirring to a pH of about 4.0 with concentrated hydrochloric acid at about 65°C. The acidified mixture is cooled to 25°C. and the precipitated reaction product, 7-amino-3-(5-methyl-1,3,4-thiadiazole-2-ylthiomethyl)-3-cephem-4-carboxylic acid, is collected by centrifugation. The product was washed with deionized water and with acetone and was then dried to yield 146 kg. of a light brown product with a purity of about 94%.

The product was slurried in 3,000 l. of deionized water and solubilized by the slow addition of a 15% caustic soda solution. The caustic soda solution was added at a rate so as to maintain the pH between 8.0 and 8.5. The solution was filtered and the filtrate loaded onto 1500 l. of IRA-458 resin in the acetate cycle covered with deionized water. Once loaded, the column was washed with 3,000 l. of deionized water. After washing the resin was eluted with potassium phosphate buffer pH 8. The elution was carried out with cooled buffer (ca 20°C.) and at a rate at which about 26 gallons-per-minute (gpm) of column effluent left the column. The effluent was checked for the presence of product by acidifying a small sample to pH 3.7 with 30% sulfuric acid. When the sample became murky white the effluent was collected.

The effluent was collected until the assay samples of effluent did not become murky on acidification. The elution with phosphate buffer was discontinued and the total eluate collected was acidified with stirring to pH 4.1 with 30% sulfuric acid at a temperature between 20° and 25°C. The precipitated product was collected on a centrifuge and washed with 600 l. of deionized water and then with 200 l. of acetone. The washed product was dried at a temperature of 70° to a moisture balance of about 2.0%. The slightly off-white dry product yield was 80% and assayed at 97% purity.

I claim:

1. The process for purifying a cephalosporin nucleus compound of the formula

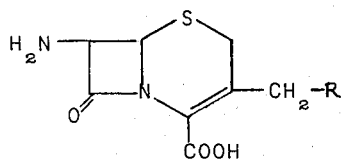

wherein R is a heterocyclic ring selected from the group consisting of

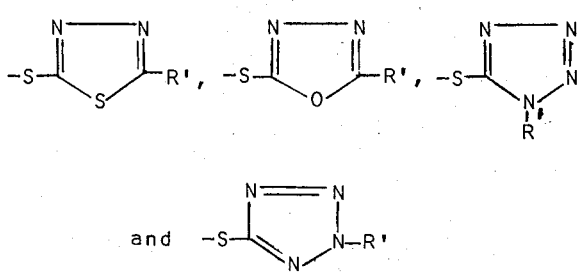

wherein R' is $C_1$–$C_4$ alkyl, which comprises adsorbing said nucleus from an aqueous solution thereof at a pH between 6.5 and 8.5 on the polyacrylic quaternary methylammoniun anion exchange resin Amberlite IRA 458; eluting said resin with phosphate buffer at a pH between 7.5 and 9.0 acidifying the eluate to a pH of between 3.5 and 5.5; and separating said nucleus in a purified form from said acidified eluate.

2. The process of claim 1 wherein the resin is in the acetate or chloride cycle.

3. The process of claim 1 wherein the resin is elated with 0.2–0.5 molar potassium phosphate buffer pH 8.

4. The process of claim 1 wherein R is the 5-methyl-1,3,4-thiadiazole-2-thio group.

5. The process of claim 1 wherein R is the 1-methyl-1H-tetrazole-5-thio group.

* * * * *